(12) United States Patent
Jan et al.

(10) Patent No.: US 8,546,630 B2
(45) Date of Patent: Oct. 1, 2013

(54) METHODS FOR REMOVING UNSATURATED ALIPHATIC HYDROCARBONS FROM A HYDROCARBON STREAM USING CLAY

(75) Inventors: Deng-Yang Jan, Elk Grove Village, IL (US); Michael A. Schultz, Glen Ellyn, IL (US); James A. Johnson, Burr Ridge, IL (US)

(73) Assignee: UOP LLC, Des Plaines, IL (US)

(*) Notice: Subject to any disclaimer, the term of this patent is extended or adjusted under 35 U.S.C. 154(b) by 90 days.

(21) Appl. No.: 13/314,749

(22) Filed: Dec. 8, 2011

(65) Prior Publication Data

US 2012/0157736 A1 Jun. 21, 2012

Related U.S. Application Data

(60) Provisional application No. 61/424,813, filed on Dec. 20, 2010.

(51) Int. Cl.
C07C 2/64 (2006.01)
C07C 7/12 (2006.01)
C07C 7/13 (2006.01)

(52) U.S. Cl.
USPC .................. 585/448; 585/822; 585/823

(58) Field of Classification Search
USPC .......................... 585/448, 822, 823
See application file for complete search history.

(56) References Cited

U.S. PATENT DOCUMENTS

| | | | |
|---|---|---|---|
| 2,438,421 A | 3/1948 | Sensel | |
| 3,670,041 A * | 6/1972 | Juhl et al. | ........... 585/258 |
| 3,755,153 A | 8/1973 | Rosback | |
| 3,761,533 A | 9/1973 | Otani | |
| 5,220,099 A | 6/1993 | Schreiner | |
| 6,106,702 A | 8/2000 | Sohn | |
| 6,225,518 B1 | 5/2001 | Sohn | |
| 6,315,816 B1 | 11/2001 | Cho | |
| 6,423,881 B1 | 7/2002 | Yang | |
| 6,500,996 B1 | 12/2002 | Brown | |
| 6,894,201 B1 | 5/2005 | Schmidt | |
| 7,205,448 B2 | 4/2007 | Gajda | |
| 2006/0270886 A1 | 11/2006 | Brown | |
| 2009/0326291 A1 | 12/2009 | Jan | |

FOREIGN PATENT DOCUMENTS

EP 2186784 A2 5/2010

OTHER PUBLICATIONS

U.S. Appl. No. 13/314,796, filed Dec. 8, 2011, Jan et al.
U.S. Appl. No. 13/314,842, filed Dec. 8, 2011, Jan et al.

* cited by examiner

*Primary Examiner* — Thuan D Dang
(74) *Attorney, Agent, or Firm* — Mark R Willis

(57) ABSTRACT

Disclosed is a method for removing unsaturated aliphatic compounds from a hydrocarbon feed stream by contacting the hydrocarbon feed stream with an adsorbent comprising clay to produce a hydrocarbon effluent stream having a lower unsaturated aliphatic content relative to the hydrocarbon feed stream. The hydrocarbon feed stream comprises an aromatic compound, a nitrogen compound, and an unsaturated aliphatic compound.

17 Claims, No Drawings

METHODS FOR REMOVING UNSATURATED ALIPHATIC HYDROCARBONS FROM A HYDROCARBON STREAM USING CLAY

CROSS-REFERENCE TO RELATED APPLICATION

This application claims the benefit of U.S. Provisional Application No. 61/424,813 filed on Dec. 20, 2010.

FIELD OF THE INVENTION

This invention relates to methods for removing unsaturated aliphatic compounds from a hydrocarbon stream. More particularly, this invention relates to use of clay adsorbents to remove unsaturated aliphatics from a hydrocarbon stream comprising aromatics.

BACKGROUND OF THE INVENTION

The use of molecular sieves as catalysts in aromatic conversion processes are well known in the chemical processing and refining industry. Aromatic conversion reactions of considerable commercial importance include the alkylation of aromatic compounds such as in the production of ethyltoluene, xylene, ethylbenzene, cumene, or higher alkyl aromatics and in disproportionation reactions such as toluene disproportionation, xylene isomerization, or the transalkylation of polyalkylbenzenes to monoalkylbenzenes. Often the feedstock to such an aromatic conversion process will include an aromatic component, i.e. alkylation substrate, such as benzene, and a C2 to C20 olefin alkylating agent or a polyalkyl aromatic hydrocarbon transalkylating agent. As used herein, terms such as "C4", "C5", "C6", etc. designate the number of carbon atoms per molecule of a hydrocarbon or hydrocarbon specie. In the alkylation zone, the aromatic feed stream and the olefinic feed stream may be reacted over an alkylation catalyst to produce alkylated aromatics, e.g. cumene or ethylbenzene. A portion or all of the alkylation substrate may be provided by other process units including the separation section of a styrene process unit. Polyalkylated benzenes are separated from monoalkylated benzene product and recycled to a transalkylation zone and contacted with benzene over a transalkylation catalyst to yield monoalkylated benzenes and benzene.

Catalysts for aromatic conversion processes generally comprise zeolitic molecular sieves. Examples include, zeolite beta (U.S. Pat. No. 4,891,458); zeolite Y, zeolite omega and zeolite beta (U.S. Pat. No. 5,030,786); X, Y, L, B, ZSM-5 and Omega crystal types (U.S. Pat. No. 4,185,040); X, Y, ultrastable Y, L, Omega, and mordenite zeolites (U.S. Pat. No. 4,774,377); and UZM-8 zeolites (U.S. Pat. No. 6,756,030and U.S. Pat. No. 7,091,390). It is known in the art that the aromatic feed stream to aromatic conversion processes often contains nitrogen compounds, including weakly basic organic nitrogen compounds such as nitriles, that can, even at ppm and ppb levels, cumulatively act to poison the downstream aromatic conversion catalysts such as aromatic alkylation catalysts and significantly shorten their useful life. A variety of guard beds having clay, zeolite, or resin adsorbents to remove one or more types of nitrogen compounds from an aromatic hydrocarbon stream upstream of an aromatic conversion process are known in the art. Examples include: U.S. Pat. Nos. 7,205,448; 7,744,828; 6,297,417; 5,220,099;WO 00/35836; WO 01/07383; U.S. Pat. Nos. 4,846,962; 6,019,887; and 6,107,535.

It has recently been discovered that unsaturated aliphatic hydrocarbons such as olefinic compounds, and particularly diolefins, can shorten the effective life of adsorbents, e.g. nitrogen adsorptive zeolites or molecular sieves, used in nitrogen guard beds that are applied to various process streams, including aromatic hydrocarbon feeds upstream of an aromatic conversion process such as alkylation. These unsaturated aliphatic, e.g. olefinic, compounds are present in aromatic process streams contaminated with nitrogen compounds, including benzene streams generated in styrene process separation sections and other streams requiring removal of the nitrogen compounds prior to being contacted with a catalyst or other material susceptible to nitrogen poisoning. The presence, in particular, of highly unsaturated olefinic compounds, e.g. C4-C6 diolefins, in aromatic streams having nitrogen compound contaminants, adversely impacts the performance of nitrogen adsorptive materials. Without being bound by theory, it is believed that the olefinic compounds and/or other unsaturated aliphatic compounds may shorten the life of the nitrogen adsorbent by competing with the nitrogen compounds for the adsorption sites and/or reacting, e.g. with aromatics such as benzene, to form heavy reaction products that deposit on the nitrogen guard bed adsorbent.

SUMMARY OF THE INVENTION

The invention relates to methods for removing unsaturated aliphatic compounds, including olefins and/or diolefins that are present in an aromatic hydrocarbon stream. In an embodiment, the invention enables longer life of the adsorbent in a downstream nitrogen removal zone, which minimizes the need to regenerate or replace the nitrogen adsorbent.

In an embodiment, the invention is a method for treating a hydrocarbon feed stream comprising an aromatic compound, a nitrogen compound, and an unsaturated aliphatic compound. The method comprises contacting the hydrocarbon feed stream with an adsorbent comprising clay, at contacting conditions comprising a temperature of at least about 50° C. and the presence of water in an amount of at least about 50 ppm relative to the hydrocarbon feed stream on a weight basis, to remove the unsaturated aliphatic compound and produce a treated hydrocarbon stream.

In another embodiment, the invention is a method for producing an alkylated benzene compound. The method comprises (i) contacting a hydrocarbon feed stream comprising benzene, an organic nitrogen compound, and a diolefin compound with an adsorbent comprising clay to remove the diolefin compound and produce a treated hydrocarbon stream; (ii) passing at least a portion of the treated hydrocarbon stream to a nitrogen removal zone, which produces an alkylation substrate stream; and (iii) passing at least a portion of the alkylation substrate stream to an alkylation zone, which produces the alkylated benzene compound.

The combination of removing one or more unsaturated aliphatic compounds and removing nitrogen from aromatic streams can extend the life of the catalyst in the alkylation zone and/or the life of an adsorbent in a nitrogen removal zone, which may be located between the unsaturated aliphatic removal zone and the alkylation zone. Further, the removal of the reactive unsaturated aliphatic hydrocarbons, such as, olefins and/or diolefins, may minimize the loss of benzene and other desired aromatic compounds to be recycled and reacted. Unexpectedly, it has been found that an adsorbent comprising clay is more selective for removing diolefins having from four to six carbon atoms per molecule than for removing the overall mixture of unsaturated aliphatic hydrocarbons in the hydrocarbon feed stream.

DETAILED DESCRIPTION OF THE INVENTION

The invention relates to methods for treating a hydrocarbon feed stream wherein one or more unsaturated aliphatic hydrocarbon compounds are removed from the feed stream by an adsorbent comprising clay to produce a treated hydrocarbon stream. The treated hydrocarbon stream has a lower unsaturated aliphatic hydrocarbon content relative to the hydrocarbon feed stream. The hydrocarbon feed stream of the invention comprises an aromatic compound, a nitrogen compound and an unsaturated aliphatic compound.

The aromatic hydrocarbon compound may be selected from the group consisting of benzene, naphthalene, anthracene, phenanthrene, and substituted derivatives thereof, with benzene and its derivatives being preferred aromatic compounds. The aromatic compound may have one or more of the substituents selected from the group consisting of alkyl groups having from 1 to about 20 carbon atoms, hydroxyl groups, and alkoxy groups whose alkyl group also contains from 1 up to 20 carbon atoms. Where the substituent is an alkyl or alkoxy group, a phenyl group can also be substituted on the alkyl chain.

Although unsubstituted and monosubstituted benzenes, naphthalenes, anthracenes, and phenanthrenes are most often used in the practice of this invention, polysubstituted aromatics also may be employed. Examples of suitable alkylatable aromatic compounds in addition to those cited above include biphenyl, toluene, xylene, ethylbenzene, propylbenzene, butylbenzene, pentylbenzene, hexylbenzene, heptylbenzene, octylbenzene, etc.; phenol, cresol, anisole, ethoxy-, propoxy-, butoxy-, pentoxy-, hexoxybenzene, and so forth. Sources of benzene, toluene, xylene, and or other feed aromatics include product streams from naphtha reforming units, aromatic extraction units, recycle streams from styrene monomer production units, and petrochemical complexes for the producing para-xylene and other aromatics. The hydrocarbon feed stream may comprise more one or more aromatic hydrocarbon compounds. In an embodiment, the concentration of the aromatic compound in the hydrocarbon feed stream ranges from about 5 wt % to about 99.9 wt % of the hydrocarbon feed. In another embodiment, the hydrocarbon feed stream comprises between about 50 wt % and about 99.9 wt % aromatics, and may comprise between about 90 wt % and about 99.9 wt % aromatics.

The hydrocarbon feed stream nitrogen compound may comprise one or more organic nitrogen compounds. Organic nitrogen compounds typically include a larger proportion of basic nitrogen compounds such as indoles, pyridines, quinolines, diethanol amine (DEA), morpholines including N-formyl-morpholine (NFM) and N-methyl-pyrrolidone (NMP). Organic nitrogen compounds may also include weakly basic nitriles, such as acetonitrile, propionitrile, and acrylonitrile. As discussed below, the instant invention does not require but encompasses use of an optional nitrogen removal zone which reduces the nitrogen content of a hydrocarbon stream.

In an embodiment, the hydrocarbon feed stream has a nitrogen content ranging from about 1 ppm-wt to about 10 ppm-wt. In another embodiment, the concentration of organic nitrogen compounds in the hydrocarbon feed ranges from about 30 ppb-wt (parts per billion by weight) to about 1 mole % of the hydrocarbon feed; the concentration of organic nitrogen compounds may range from about 100 ppb-wt to about 100 ppm-wt (parts per million by weight) of the hydrocarbon feed. In an embodiment, the concentration of weakly basic organic nitrogen compounds such as nitriles in the hydrocarbon feed ranges from about 30 ppb-wt to about 100 ppm-wt of the hydrocarbon feed.

The hydrocarbon feed stream comprises one or more unsaturated aliphatic compounds, including unsaturated cyclic hydrocarbons and straight and branched chain olefinic hydrocarbons (olefins) having one or more double bonds. Thus, as used herein the terms "olefins" and "olefinic hydrocarbons" include diolefin compounds. In an embodiment, the unsaturated aliphatic compound is an olefin compound, and the unsaturated aliphatic compound may be a diolefin compound. In an embodiment, the unsaturated aliphatic compound is one or more diolefin compounds having four, five, or six carbon atoms per molecule, i.e. the unsaturated aliphatic compound may be selected from the group of diolefins consisting of C4 diolefins, C5 diolefins, C6 diolefins, and mixtures thereof. In another embodiment, the diolefin compound is selected from the group consisting of butadienes, pentadienes, methylbutadienes, hexadienes, methylpentadienes, dimethylbutadienes, acetylenes, and mixtures thereof.

In an embodiment, the concentration of diolefin compounds in the hydrocarbon feed ranges from about 30 ppb-wt to about 3000 ppm-wt of the hydrocarbon feed; and the concentration of diolefin compounds may range from about 50 ppb-wt to about 2000 ppm-wt of the hydrocarbon feed. The hydrocarbon feed stream may comprise other olefins such as mono-olefins. Typically, the overall concentration of all olefins in the hydrocarbon feed stream will be no more than 1.0 wt-% olefins.

In an embodiment, the aromatic compound comprises benzene, the nitrogen compound comprises an organic nitrogen compound, and the unsaturated aliphatic compound comprises an olefin compound. In another embodiment, the aromatic compound comprises benzene, the nitrogen compound comprises an organic nitrogen compound, and the unsaturated aliphatic compound comprises a diolefin compound, optionally the diolefin compound has four to six carbon atoms per molecule.

The adsorbent used in the instant invention comprises clay. Suitable clays include for example, beidellite, hectorite, laponite, montmorillonite, nontonite, saponite, bentonite, and mixtures thereof. Examples of suitable, commercially available, clay adsorbents include F-Series adsorbents available from BASF and TONSIL adsorbents such as CO 630 G and CO 616 GS available from Sud-Chemie. In an embodiment, the clay adsorbent is an acid activated bentonite and/or montmorillonite clay.

The hydrocarbon feed stream to be treated is contacted with a clay adsorbent at contacting conditions to remove one or more unsaturated aliphatic compounds and produce a treated hydrocarbon stream. The unsaturated aliphatic compounds may be removed from the hydrocarbon stream by various mechanisms such as adsorption, reaction, and reactive adsorption with the adsorbent. The treated hydrocarbon stream has a lower unsaturated aliphatic compound content relative to the unsaturated aliphatic compound content of the hydrocarbon feed stream.

The contacting conditions include a temperature of at least about 50° C. and the presence of water in an amount of at least about 50 ppm relative to the hydrocarbon feed stream on a weight basis. Water may be present in an amount equal to or beyond the saturation point of the hydrocarbon feed stream at the contacting conditions. In an embodiment, water is present in an amount of at least about 250 ppm relative to the hydrocarbon feed stream on a weight basis. In another embodiment, water is present in an amount ranging from about 300 ppm to about 800 ppm relative to the hydrocarbon feed stream on a weight basis, and water may be present in an amount ranging from about 450 ppm to about 700 ppm relative to the hydrocarbon feed stream on a weight basis. The amount of water during contacting may be controlled in any suitable manner. For example, the water content of the hydrocarbon feed may be monitored and controlled by drying and/or adding water or water generating compounds to the feed stream. Water or water generating compounds may be introduced as a separate stream to the contacting step, and the feed stream may be dried to a consistent water level while water or water generating compounds are added to obtain the desired content. In an embodiment, the contacting temperature ranges from about 50° C. to about 300° C. and the contacting temperature may range from about 50° C. to about 125° C. In another embodiment, the contacting temperature ranges from about 75° C. to about 250° C.; and the contacting temperature may range from about 100° C. to about 225° C.

In an embodiment, the amount of water is at least about 50 ppm relative to the hydrocarbon feed stream on a weight basis and the contacting temperature: (i) is at least about 50° C.; (ii) ranges from about 50° C. to about 300° C.; (iii) ranges from about 50° C. to about 125° C.; (iv) ranges from about 75° C. to about 250° C.; or (v) ranges from about 100° C. to about 225° C. In an embodiment, the amount of water is at least about 250 ppm relative to the hydrocarbon feed stream on a weight basis and the contacting temperature: (i) is at least about 50° C.; (ii) ranges from about 50° C. to about 300° C.; (iii) ranges from about 50° C. to about 125° C.; (iv) ranges from about 75° C. to about 250° C.; or (v) ranges from about 100° C. to about 225° C. In another embodiment, the amount of water equals or exceeds the saturation point of the hydrocarbon feed stream at the contacting conditions and the contacting temperature: (i) is at least about 50° C.; (ii) ranges from about 50° C. to about 300° C.; (iii) ranges from about 50° C. to about 125° C.; (iv) ranges from about 75° C. to about 250° C.; or (v) ranges from about 100° C. to about 225° C. In a further embodiment, the amount of water ranges from about 300 ppm to about 800 ppm relative to the hydrocarbon feed stream on a weight basis and the contacting temperature: (i) is at least about 50° C.; (ii) ranges from about 50° C. to about 300° C.; (iii) ranges from about 50° C. to about 125° C.; (iv) ranges from about 75° C. to about 250° C.; or (v) ranges from about 100° C. to about 225° C. In an embodiment, the amount of water ranges from about 450 ppm to about 700 ppm relative to the hydrocarbon feed stream on a weight basis and the contacting temperature: (i) is at least about 50° C.; (ii) ranges from about 50° C. to about 300° C.; (iii) ranges from about 50° C. to about 125° C.; (iv) ranges from about 75° C. to about 250° C.; or (v) ranges from about 100° C. to about 225° C. Optionally, the contacting conditions may further include a pressure from about 34.5 kPa(g) to about 4136.9 kPa(g). In an embodiment, the contacting is conducted with the feed in the liquid phase or partial liquid phase. Gas phase contacting may be used.

Bromine Index is commonly used to assess the unsaturated aliphatic content, including olefins and diolefins, of hydrocarbon mixtures. In an embodiment, the invention removes at least about 50% of the unsaturated aliphatic compounds from the hydrocarbon feed stream. That is, in this embodiment, the treated hydrocarbon stream has a Bromine Index of at most about 50% of the Bromine Index of the hydrocarbon feed stream. As used herein the Bromine Index of the hydrocarbon streams or mixtures is determined using method UOP304. In another embodiment, the invention removes at least about 70 wt % of the diolefin compounds from the hydrocarbon feed stream; and the invention may remove at least about 90 wt % or at least about 95 wt % of the diolefin compounds from the hydrocarbon feed stream. Herein, the diolefin content of the hydrocarbon streams or mixtures is determined by method UOP980. Unless otherwise noted, the analytical methods used herein such as UOP304 and UOP980 are available from ASTM International, 100 Barr Harbor Drive, West Conshohocken, Pa., USA.

In another embodiment, the invention further comprises passing at least a portion of the treated hydrocarbon stream to a nitrogen removal zone, the nitrogen removal zone producing an alkylation substrate stream having a lower concentration of the nitrogen compound relative to the treated hydrocarbon stream. As discussed above, various methods are well known in the art to remove nitrogen compounds from aromatic hydrocarbon streams. See, for example, U.S. Pat. Nos. 7,205,448; 7,744,828; 6,297,417; each of which is herein incorporated by reference in its entirety. In brief, the treated hydrocarbon stream is introduced to the nitrogen removal zone which includes at least one adsorbent effective to remove nitrogen. Suitable adsorbents include clays, resins, and zeolites. Typically, the clay and zeolite adsorbents are acidic. The nitrogen removal zone may comprise two adsorbents such as a clay or resin adsorbent being located upstream of a zeolite adsorbent so the treated hydrocarbon stream contacts the clay or resin adsorbent first to produce an intermediate stream which then contacts the zeolite adsorbent. Different operating conditions including temperatures and the amount of water present have been disclosed for different adsorbents and the use of multiple adsorbents in the nitrogen removal zone.

In an embodiment, the treated hydrocarbon stream is contacted with an adsorbent comprising an acidic molecular sieve at nitrogen removal conditions to produce the alkylation substrate stream having a reduced nitrogen content. In an embodiment the molecular sieve is a zeolite. Well known zeolites that may be used include chabazite, also referred to as Zeolite D, clinoptilolite, erionite, faujasite, Zeolite Beta (BEA), Zeolite Omega, Zeolite X, Zeolite Y, MFI zeolite, Zeolite MCM-22 (MWW), ferrierite, mordenite, Zeolite A, Zeolite P, and UZM-8 type zeolites referenced below. In an embodiment, the nitrogen removal conditions comprise a temperature ranging from at least about 120° C. to about 300° C., and the presence of water in an amount ranging from about 20 ppm to about 500 ppm relative to the treated hydrocarbon stream on a weight basis.

In another embodiment, the invention further comprises passing at least a portion of the alkylation substrate stream from the nitrogen removal zone to an alkylation zone wherein the portion of the alkylation substrate stream and an alkylating agent are contacted with an alkylation catalyst to produce an alkylated benzene product.

In the selective alkylation of aromatics alkylation substrate by an olefinic alkylating agent as catalyzed by an acidic catalyst, the olefins may contain from 2 up to at least 20 carbon atoms, and may be branched or linear olefins, either terminal or internal olefins. Thus, the specific nature of the olefin is not particularly important. What the alkylation reactions share in common is that the reactions are conducted under at least partially liquid phase conditions, a criterion readily achieved for the lower members by adjusting reaction pressures. Among the lower olefins, ethylene and propylene are the most important representatives. An olefinic feed stream comprising an alkylating agent may include ethylene and/or propylene. Typically, an olefinic feed stream comprising propylene will be at least 65 wt % pure and an olefinic feed stream comprising ethylene will be over 80 wt % pure.

Among the remaining olefins, the class of detergent range olefins consisting of linear olefins containing from 6 up through about 20 carbon atoms which have either internal or terminal unsaturation is of particular interest. Linear olefins containing from 8 to 16 carbon atoms and especially those containing from 10 up to about 14 carbon atoms are particularly useful as detergent range olefins. Alkylation agents may also be provided by alkyl constituents of a polyalkylbenzene in a transalkylation reaction zone. Diethylbenzene, triethylbenzene and diisopropylbenzene are prominent examples of polyalkylbenzenes that can provide such alkylation agents.

A wide variety of catalysts can be used in the alkylation reaction zone. Suitable catalysts for use in the alkylation zone include catalysts that do not suffer deleterious effects from the presence of water. Preferably, a substantial quantity of water may be tolerated or desired in the presence of the alkylation catalyst. A substantial quantity of water preferably means a water concentration in the reactants entering the alkylation zone of at least 50 wppm. The alkylation reaction zone may have a water content of as little as 20 wppm, to over 200 wppm and up to 1000 wppm or more. The preferred catalyst for use in this invention is a zeolitic catalyst. The catalyst of this invention will usually be used in combination with a refractory inorganic oxide binder. Preferred binders are alumina or silica. Suitable zeolites include zeolite beta described in U.S. Pat. No. 5,723,710, ZSM-5, PSH-3, MCM-22, MCM-36, MCM-49, MCM-56, type Y zeolite, and UZM-8, which includes the aluminosilicate and substituted aluminosilicate zeolites described in U.S. Pat. No. 6,756,030 and the modified UZM-8 zeolites, such as, UZM-8HS which are described in U.S. Pat. No. 7,091,390. Each of U.S. Pat. No. 6,756,030 and U.S. Pat. No. 7,091,390 is herein incorporated by reference in its entirety.

The basic configuration of a catalytic aromatic alkylation zone is known in the art. The feed aromatic alkylation substrate and the feed olefin alkylating agent are preheated and charged to generally from one to four reactors in series. Suitable cooling means may be provided between reactors to compensate for the net exothermic heat of reaction in each of the reactors. Suitable means may be provided upstream of or with each reactor to charge additional feed aromatic, feed olefin, or other streams (e.g., effluent of a reactor, or a stream containing one or more polyalkylbenzenes) to any reactor in the alkylation zone. Each alkylation reactor may contain one or more alkylation catalyst beds. The invention encompasses dual zone aromatic alkylation processes such as those as described in U.S. Pat. No. 7,420,098 which is herein incorporated by reference in its entirety.

The particular conditions under which the alkylation reaction is conducted depends upon the aromatic compound and the olefin used. One necessary condition is that the reaction be conducted under at least partial liquid phase conditions. Therefore, the reaction pressure is adjusted to maintain the olefin at least partially dissolved in the liquid phase. For higher olefins the reaction may be conducted at autogenous pressure. The alkylation conditions usually include a pressure in the range between about 1379 kPa(g) and 6985 kPa(g). In an embodiment, the pressure ranges between about 2069 kPa(g) and 4137 kPa(g). The alkylation of the aromatic compounds with the olefins in the C2 to C20 range can be carried out at a temperature of about 60° C. to about 400° C., and preferably from about 90° C. to about 250° C., for a time sufficient to form the desired product. In a continuous process this time can vary considerably, but is usually from about 0.1 to about 8 hr$^{-1}$ weight hourly space velocity (WHSV) with respect to the olefin. As used herein, weight hourly space velocity of a component means the weight flow rate of the component per hour divided by the catalyst weight in the same units of measure. In particular, the alkylation of benzene with ethylene can be carried out at temperatures of about 150° C. to about 250° C. and the alkylation of benzene with propylene at a temperature of about 90° C. to about 200° C. The ratio of alkylatable aromatic compound to olefin used in the instant process will depend upon the degree of monoalkylation desired as well as the relative costs of the aromatic and olefinic components of the reaction mixture. For alkylation of benzene by propylene, the benzene-to-olefin molar ratio may be as low as about 0.1 and as high as about 10, with a ratio of about 0.5 to about 3 being preferred. Where benzene is alkylated with ethylene a benzene-to-olefin ratio may be between about 0.1 and 10, with a ratio of about 0.5 to about 4 being preferred. For detergent range olefins of C6 to C20, a benzene-to-olefin ratio of between about 5 and about 30 is generally sufficient to obtain the desired monoalkylation yield, with a range between about 8 and about 20 even more preferred.

The alkylation reaction zone will often provide a wide variety of secondary by-products. For example, in the alkylation of benzene with ethylene to produce ethylbenzene, the reaction zone can also produce di- and triethylbenzene in addition to other ethylene condensation products. Similarly, in the alkylation of benzene with propylene to produce cumene, the reaction zone can produce di- and triisopropylbenzene in addition to still more condensation products. As is well known in the art, these polyalkylated aromatics may contact additional aromatic substrate in a transalkylation zone to produce additional monoalkylated product. See e.g. U.S. Pat. No. 7,622,622 and U.S. Pat. No. 7,268,267. Further, since transalkylation reactions occur in an alkylation reaction zone and alkylation reactions occur in a transalkylation reaction zone, both zones may be referred to as alkylation zones. Thus, as used herein, the term "alkylation zone" encompasses a transalkylation zone. In an embodiment, the alkylated benzene product comprises at least one of ethylbenzene and cumene.

In a further embodiment, the invention is a method for producing an alkylated benzene compound. The method comprises contacting a hydrocarbon feed stream comprising benzene, an organic nitrogen compound, and a diolefin compound with an adsorbent comprising clay. Optionally, the diolefin compound has from four to six carbon atoms per molecule. Contacting conditions comprise a temperature of at least about 50° C. and the presence of water in an amount of at least about 50 ppm relative to the hydrocarbon feed stream on a weight basis. The contacting step removes the diolefin compound and produces a treated hydrocarbon stream having a lower concentration of the diolefin compound than the hydrocarbon feed stream. At least a portion of the treated hydrocarbon stream is passed to a nitrogen removal zone, which removes the organic nitrogen compound and produces an alkylation substrate stream having a lower concentration of the organic nitrogen compound relative to the treated hydrocarbon stream. At least a portion of the alkylation substrate stream is passed to an alkylation zone wherein the portion of the alkylation substrate stream and an alkylating agent are contacted with an alkylation catalyst to produce an alkylated benzene compound. In an embodiment, the alkylated benzene compound is a monoalkylated benzene compound, which may comprise at least one of ethylbenzene and cumene.

EXAMPLE 1

An adsorbent for use according to the invention is a commercially available acid treated clay that was obtained from Sud-Chemie under the product name TONSIL CO 630 G.

EXAMPLE 2

As a comparative example, a commercially available activated carbon was obtained from Calgon.

EXAMPLE 3

As a comparative example, a sample of a steam modified ammonium ion exchanged Y zeolite was slurried in a 15 wt % $NH_4NO_3$ aqueous solution and the solution temperature was brought up to 75° C. (167° F.). The steam modified ammonium ion exchanged Y zeolite is a stabilized sodium Y zeolite with a bulk $Si/Al_2$ ratio of approximately 5.2, a unit cell size of approximately 24.53, and a sodium content of approximately 2.7 wt % calculated as $Na_2O$ on a dry basis. The steam modified ammonium ion exchanged Y zeolite is prepared from a sodium Y zeolite with a bulk $Si/Al_2$ ratio of approximately 4.9, a unit cell size of approximately 24.67, and a sodium content of approximately 9.4 wt % calculated as $Na_2O$ on a dry basis that is ammonium exchanged to remove approximately 75% of the Na and then steam de-aluminated at approximately 600° C. (1112° F.) by generally following steps (1) and (2) of the procedure described in col. 4, line 47 to col. 5, line 2 of U.S. Pat. No. 5,324,877. After 1 hour of contact at 75° C. (167° F.), the slurry was filtered and the filter cake was washed with an excessive amount of warm de-ionized water. These $NH_4^+$ ion exchange, filtering, and water wash steps were repeated two more times, and the resulting filter cake had a bulk $Si/Al_2$ ratio of 5.2, a sodium content of 0.13 wt % calculated as $Na_2O$ on a dry basis, a unit cell size of the 24.572 Å and an absolute intensity of 96 as determined X-ray diffraction. The resulting filter cake was dried to an appropriate moisture level, mixed with $HNO_3$-peptized Pural SB alumina to give a mixture of 80 parts by weight of zeolite and 20 parts by weight $Al_2O_3$ binder on a dry basis, and then extruded into 1.6 mm diameter cylindrical extrudate. The extrudate was dried and calcined at approximately 600° C. for one hour in flowing air to obtain a comparative zeolite adsorbent having a unit cell size of 24.494 Å, an XRD absolute intensity of 61.1, and 57.2% framework aluminum as a percentage of the aluminum in the modified Y zeolite.

EXAMPLE 4

A sample of a commercial benzene recycle stream (>99 wt % benzene) containing olefin, diolefin and nitrogen compounds was used as is without drying or other treatments as the hydrocarbon feed to evaluate the effectiveness of the adsorbents of Examples 1-3 to remove the unsaturated aliphatic compounds. The analysis of the feed is reported in Table 1 with the analysis of the effluent or product from each test. The unsaturated aliphatic content was determined by Bromine Index method UOP304. The diolefin content was determined by UOP980 as modified to improve the sensitivity of the method to detect lower levels of diolefins. UOP980 was followed except that sample size was altered and standard solutions of lower concentrations were used during calibration of the instrument as known by those skilled in the art to improve detection of lower concentrations of the diolefins in the samples. The modification of UOP980 does not alter the relative measurements between different samples, but improves and/or enables quantification of concentrations of less than 500 ppm-wt and especially less than 100 ppm-wt of diolefins. The commercial benzene recycle stream also included water at about the saturation level so the contacting conditions included an amount of water ranging from about 600 ppm to about 800 ppm relative to the hydrocarbon feed stream on a weight basis.

Prior to the test, the adsorbent was pre-dried at 250° C. for 4 hours in flowing nitrogen. The adsorption experiment was done in an autoclave, which was first purged with nitrogen followed by charging 0.6 g of adsorbent and 30 g of the hydrocarbon feed. The autoclave was then pressurized to about 400 psig and ramped to the temperature listed in Table 1 for each test. The autoclave includes a mixer which was set at 100 rpm. When the specified temperature was reached, the autoclave was held at temperature for one hour with mixing. Thereafter, the heat was cut to allow the autoclave to cool to room temperature and mixing stopped. The spent adsorbent was separated from the liquid product or effluent, which was sampled and analyzed.

TABLE 1

| | Feed | Example 1 | | | Example 2 | | | Example 3 | | |
|---|---|---|---|---|---|---|---|---|---|---|
| Temperature, ° C. | | 100 | 125 | 150 | 100 | 125 | 150 | 25 | 75 | 125 |
| Bromine Index, mg Br per 100 g | 292 | 138 | 91 | 47 | 189 | 138 | NA | 114 | 91 | 23 |
| Diolefins, ppm-wt | 825 | 25 | 3 | 1 | 550 | 340 | 92 | NA | 247 | 5 |
| Unsaturated aliphatics removed, % based on Bromine Index | | 53 | 69 | 84 | 35 | 53 | NA | 61 | 69 | 92 |
| Diolefins removed, wt % | | 97 | 99.6 | 99.9 | 33 | 59 | 89 | NA | 70 | 99.4 |

The data demonstrate, each material of Examples 1-3 is effective for removing unsaturated aliphatic hydrocarbons, as determined by Bromine Index, and for removing diolefins. The clay adsorbent of Example 1 according to the invention, exhibited unexpected selectivity and stability in removing diolefins. At each temperature evaluated, the clay adsorbent exhibited significantly greater diolefin removal compared to the removal of unsaturated aliphatic thus demonstrating a higher selectivity for removing diolefins relative to the general class of unsaturated aliphatic compounds. Surprisingly, the amount of diolefins removed by the clay adsorbent of Example 1 was largely unaffected over the temperature range evaluated.

The invention claimed is:

1. A method for treating a hydrocarbon feed stream comprising an aromatic compound, a nitrogen compound, and an unsaturated aliphatic compound, the method comprising: contacting the hydrocarbon feed stream with an adsorbent comprising clay at contacting conditions including a temperature of at least about 25° C. and the presence of water in an amount of at least about 50 ppm relative to the hydrocarbon feed stream on a weight basis to remove the unsaturated aliphatic compound and produce a treated hydrocarbon stream;

passing at least a portion of the treated hydrocarbon stream to a nitrogen removal zone including a nitrogen removal adsorbent to produce an alkylation substrate stream having a lower concentration of the nitrogen compound relative to the treated hydrocarbon stream; and passing at least a portion of the alkylation substrate stream to an alkylation zone wherein the portion of the alkylation substrate stream and an alkylating agent are contacted with an alkylation catalyst to produce an alkylated aromatic compound.

2. The method of claim 1 wherein water is present in an amount equal to or exceeding the saturation point of the hydrocarbon feed stream at the contacting conditions.

3. The method of claim 1 wherein water is present in an amount of at least about 250 ppm relative to the hydrocarbon feed stream on a weight basis.

4. The method of claim 1 wherein the temperature ranges from about 50° C. to about 300° C.

5. The method of claim 1 wherein the temperature ranges from about 50° C. to about 125° C.

6. The method of claim 1 wherein the contacting conditions further include a pressure ranging from about 34.5 kPa(g) to about 4136.9 kPa(g).

7. The method of claim 1 wherein the hydrocarbon feed stream has a nitrogen content ranging from about 1 ppm-wt to about 10 ppm-wt.

8. The method of claim 1 wherein the aromatic compound is benzene and is present in an amount ranging from about 5 wt % to about 99.9 wt % of the hydrocarbon feed stream.

9. The method of claim 1 wherein the nitrogen compound is an organic nitrogen compound selected from the group consisting of basic organic nitrogen compounds, nitriles, and mixtures thereof.

10. The method of claim 9 wherein the organic nitrogen compound is present in an amount ranging from about 30 ppb-wt to about 1 mole % of the hydrocarbon feed stream.

11. The method of claim 1 wherein the unsaturated aliphatic compound is a diolefin compound.

12. The method of claim 11 wherein the diolefin compound is selected from the group consisting of butadienes, pentadienes, methylbutadienes, hexadienes, methylpentadienes, dimethylbutadienes, acetylenes, and mixtures thereof.

13. The method of claim 11 wherein the diolefin compound is selected from the group of diolefins consisting of C4 diolefins, C5 diolefins, C6 diolefins and mixtures thereof.

14. The method of claim 13 wherein the diolefin compound is present in an amount ranging from about 30 ppb-wt to about 3000 ppm-wt of the hydrocarbon feed stream.

15. The method of claim 13 wherein at least about 70 wt % of the diolefin compound is removed from the hydrocarbon feed stream on a weight basis.

16. The method of claim 1 wherein the treated hydrocarbon stream has a Bromine Index of at most about 50% of the Bromine Index of the hydrocarbon feed stream.

17. The method of claim 1 wherein the alkylated aromatic compound comprises at least one of ethylbenzene and cumene.

* * * * *